United States Patent [19]

Genovese

[11] Patent Number: 5,204,538
[45] Date of Patent: Apr. 20, 1993

[54] DENSITOMETER FOR AN ELECTROPHOTOGRAPHIC PRINTER USING FOCUSED AND UNFOCUSED REFLECTING BEAMS

[75] Inventor: Frank C. Genovese, Fairport, N.Y.
[73] Assignee: Xerox Corporation, Stamford, Conn.
[21] Appl. No.: 884,977
[22] Filed: May 18, 1992
[51] Int. Cl.⁵ .............................................. G01N 21/86
[52] U.S. Cl. ..................................... 250/571; 356/448
[58] Field of Search ..................... 250/571, 572, 559; 356/445, 446, 448, 443, 444; 355/37, 38

[56] References Cited

U.S. PATENT DOCUMENTS

| | | | |
|---|---|---|---|
| 3,892,492 | 7/1975 | Eichenberger | 250/571 |
| 4,553,033 | 11/1985 | Hubble, III et al. | 250/353 |
| 4,750,838 | 6/1988 | De Wolf et al. | 356/445 |
| 4,755,058 | 7/1988 | Shaffer | 356/446 |
| 4,796,065 | 1/1989 | Kanbayashi | 355/14 |
| 4,799,082 | 1/1989 | Suzuki | 355/14 R |
| 4,801,980 | 1/1989 | Arai et al. | 355/14 D |
| 4,989,985 | 2/1991 | Hubble, III et al. | 356/445 |
| 5,078,497 | 1/1992 | Borton et al. | 356/445 |
| 5,083,161 | 1/1992 | Borton et al. | 355/208 |
| 5,122,672 | 6/1992 | Mansour | 250/571 |

Primary Examiner—David C. Nelms
Assistant Examiner—Que T. Le
Attorney, Agent, or Firm—R. Hutter

[57] ABSTRACT

An apparatus measures the reflectivity of a selected region of a surface. A first light beam is reflected from the selected region and substantially focused on a photodetector. A second light beam is reflected from the selected region and is substantially unfocused on the photodetector. A signal is derived representative of the direct reflectance of light reflected from the surface onto the photodetector as a function of the intensities of the focused light beam and the unfocused light beam detected by the photodetector.

16 Claims, 5 Drawing Sheets

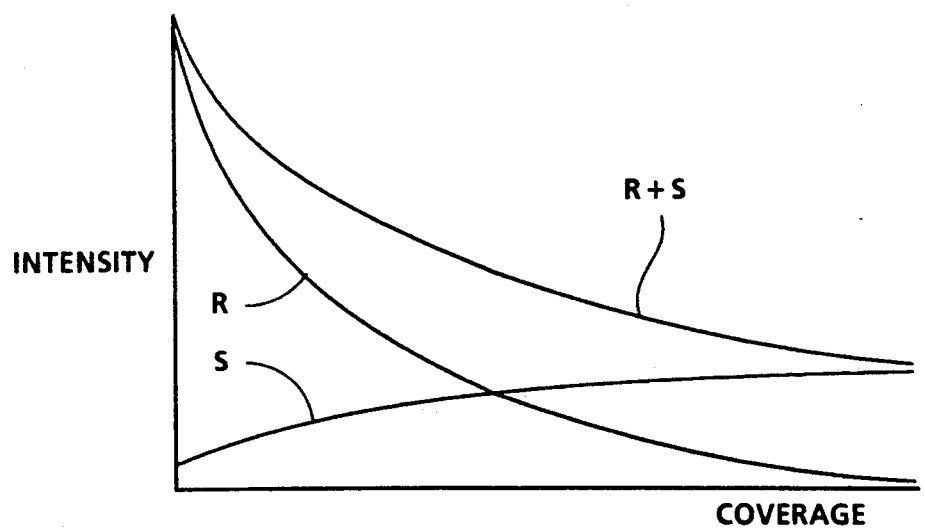
FIG. 3
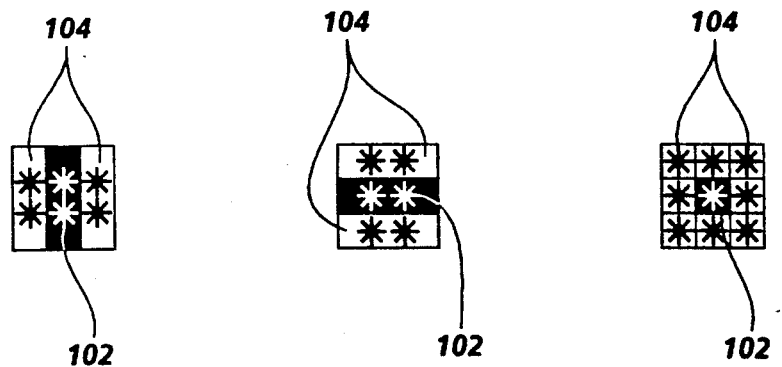
FIG. 4A  FIG. 4B  FIG. 4C
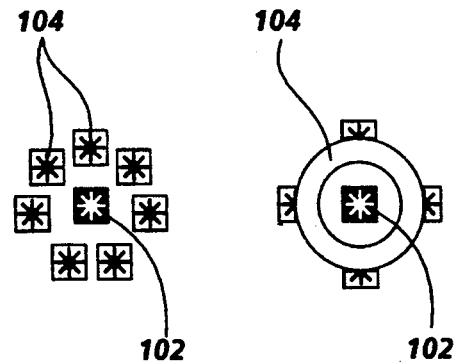
FIG. 4D  FIG. 4E

DENSITOMETER FOR AN ELECTROPHOTOGRAPHIC PRINTER USING FOCUSED AND UNFOCUSED REFLECTING BEAMS

FIELD OF THE INVENTION

The present invention relates to a densitometer for measuring toner area coverage on a photoreceptor surface in an electrophotographic printer. More specifically, the present invention relates to the use of multiple light sources and a single photodetector in such a densitometer.

BACKGROUND OF THE INVENTION

In an electrophotographic printing machine, the photoconductive member is charged to a substantially uniform potential to sensitize the surface thereof. The charged portion of the photoconductive member is exposed to a light image of an original document being reproduced. Exposure of the charged photoconductive member selectively dissipates the charge thereon in the irradiated areas. This records an electrostatic latent image on the photoconductive member corresponding to the informational areas contained within the original document being reproduced. After the electrostic latent image is recorded on the photoconductive member, the latent image is developed by bringing marking or toner particles into contact therewith. This forms a powder image on the photoconductive member which is subsequently transferred to a copy sheet. The copy sheet is heated to permanently affix the marking particles thereto in image configuration.

Various types of development systems have hereinbefore been employed. These systems utilize two component developer mixes or single component developer materials. Typical two component developer mixes employed are well known in the art, and generally comprise dyed or colored thermoplastic powders, known in the art as toner particles, which are mixed with coarser carrier granules, such as ferromagnetic granules. The toner particles and carrier granules are selected such that the toner particles acquire the appropriate charge relative to the electrostatic latent image recorded on the photoconductive surface. When the developer mix is brought into contact with the charged photoconductive surface the greater attractive force of the electrostatic latent image recorded thereon causes the toner particles to transfer from the carrier granules and adhere to the electrostatic latent image.

Multi-color electrophotographic printing is substantially identical to the foregoing process of black and white printing. However, rather than forming a single latent image on the photoconductive surface, successive latent images corresponding to different colors are recorded thereon. A light-lens optical system or a raster input scanner (RIS)/raster output scanner (ROS) system may be used to selectively discharge the charged portion of the photoconductive surface to record the repective latent images thereon. Each single color electrostatic latent image is developed with toner particles of a color complimentary thereto. This process is repeated a plurality of cycles for differently colored images and their respective complimentarily colored toner particles. For example, a red light image is developed with cyan toner particles, while a green light image is developed with magenta toner particles and a blue light image with yellow toner particles. Each single color toner powder image is transferred to the copy sheet superimposed over the prior toner powder image. This creates a multi-layered toner powder image on the copy sheet. Thereafter, the multi-layered toner powder image is permanently affixed to the copy sheet creating a color copy. An illustrative electrophotographic printing machine for producing color copies is the Model No. 5775 made by the Xerox Coporation.

It is evident that in printing machines of this type, toner particles are depleted from the developer mixture. As the concentration of toner particles decreases, the density of the resultant copy degrades. In order to maintain the copies being reproduced at a specified minimum density, it is necessary to regulate the concentration of toner particles in the developer mixture. This is achieved by a closed loop servo system which regulates developability. Developability, as it pertains to an electrophotographic printing machine is the ability of the developer mixture to develop the latent image with at least a minimum specified density. It has long been recognized that a closed loop system, which regulates developability by measuring the density of the powder image developed on the photoconductive surface, optimizes cost and performance. This is possible because of the relative stability of the other steps in the imaging process such as transfer and fusing. Also, by modulating one parameter, such as toner particle concentration, compensation for factors contributing to low copy quality, such as photoreceptor dark decay fluctuation and developer aging, can be partially accomplished. The use of densitometers for measuring the optical density of black toner particles is well known. However, densitometers used for black toner particles are generally unsuitable for use with colored toner particles because they are generally sensitive to the large component of diffusely reflected flux in the infrared light from colored toner particles, which gives false density measurements.

In measuring the density of toner on a photoreceptor surface, even in the case of black toner, a crucial consideration is the ability to measure the specularly reflected light from the surface of the partially covered photoreceptor, while excluding light reflected as a result of the reflectivity of the toner itself. Generally, no matter what the color of a particular type of toner, the more densely the toner is applied to the photoreceptor, the "darker" (more absorptive, less reflective) the toner will appear on the photoreceptor up to some maximum saturation value. When the purpose of a densitometer is to measure the density of toner on a surface, the most important measured value is the light directly reflected from the surface, which is the difference between the light transmitted to the surface and the light blocked by the toner. However, because toner is not only absorptive but partially reflects light itself, a quantity of "scattered" or "diffuse" light will be returned to the detector from the toner as well. The light scattered by the toner itself will interfere with a reading of that blocked by the toner. Thus, it is desired that a system be devised to measure only the fraction of light blocked by toner on the photoreceptor surface, without interference from the scattered light reflecting from the toner itself, which can be considered a type of noise.

Various approaches have been used to measure directly-reflected light from toner on a surface, in order to infer therefrom the absorption of light and therefore toner density. The following disclosures appear to be relevant:

U.S. Pat. No. 4,553,033. Patentee: Hubble, III et al. Issued: Nov. 12, 1985.

U.S. Pat. No. 4,750,838. Patentee: DeWolf et al. Issued: Jun. 14, 1988.

U.S. Pat. No. 4,796,065. Patentee: Kanbayashi. Issued: Jan. 3, 1989.

U.S. Pat. No. 4,799,082. Patentee: Suzuki. Issued: Jan. 17, 1989.

U.S. Pat. No. 4,801,980. Patentee: Arai et al. Issued: Jan. 31, 1989.

U.S. Pat. No. 4,989,985. Patentee: Hubble, III et al. Issued: Feb. 5, 1991.

U.S. Pat. No. 5,083,161. Patentee: Borton et al. Issued: Jan. 21, 1992.

The relevant portions of the foregoing patents may be briefly summarized as follows:

U.S. Pat. No. 4,553,033 discloses an infrared reflectance densitometer including a light emitting diode, a collimating lens through which light is projected to a photosensitive surface, a collector lens and a field lens through which reflected light is focused onto a signal photodiode, and a control photodiode onto which a portion of reflected light is directed to control light output. The amount of light received on the signal photodiode is a measurement of the reflectance from the surface of the photoreceptor which, in turn, is proportional to the density of the toner particles thereon.

U.S. Pat. No. 4,750,838 describes an optoelectric circuit for measuring differences in optical densities of an image carrier. An LED illuminates a test area. The light reflected from the surface is sensed by a phototransistor. The linear output of the LED is proportional to the image density. The circuit has a voltage follower, output transistor, amplifier and differential amplifier for controlling the image density measurements. The circuit has a range of density sensitivities between 0.0 and 1.5 mg/cm$^2$.

U.S. Pat. No. 4,796,065 discloses an apparatus for detecting image density in an image forming machine by sensing either regular reflection or scattered reflection. A circuit having light emitting elements (LEDs or phototransistors), a pair of sensors, and a comparator is used for determining image density.

U.S. Pat. No. 4,799,082 describes an electrostatic reproducing apparatus having a light source and detector for detecting color toner density. A sensor is driven by a circuit which contains a power source, a safety resistor, operational amplifier, comparator and voltage dividing resistors for producing a signal reprsentative of the light reflected from the image.

U.S. Pat. No. 4,801,980 discloses a toner density control apparatus which compares an image density of a reference image with a predetermined level to control density. Voltage to a light emitting element is controlled by the circuit which includes a sensor correction portion.

U.S. Pat. No. 4,989,985 describes an infrared densitometer which measures the reduction in the specular component of reflectivity as toner particles are progressively deposited on a moving photoconductive belt. Collimated light rays are projected onto the toner particles. The light rays reflected from at least the toner particles are collected and directed onto a photodiode array. The photodiode array generates electrical signals proportional to the total flux and the diffuse component of the total flux of the reflected light rays. Circuitry compares the electrical signals and determines the difference therebetween to generate an electrical signal proportional to the specular component of the total flux of the reflected light rays.

U.S. Pat. No. 5,083,161 describes an infrared densitometer which measures the reflectivity of a selected region on a surface by reflecting light rays from a single source off the selected region onto an array of photodiodes.

SUMMARY OF THE INVENTION

According to the present invention, an apparatus measures the reflectivity of a selected region of a surface. A pair of light beams are reflected from the selected region of the surface. A photodetector is so arranged that one of the pair of beams is focused thereon so that the photodetector senses focused reflected light, while the other of the pair of light beams reflected from the selected region is unfocused thereon so that the photodetector senses unfocused reflected light. A processor derives a signal representative of the direct reflectance of light reflected from the surface onto the photodetector as a function of the intensities of the focused light beam and the unfocused light beam detected by the photodetector.

Also according to the present invention, there is provided a method for measuring the reflectivity of a selected region of a surface. A pair of light beams are reflected from the selected region of the surface. Focused light is detected from one of the pair of light beams and unfocused light from the other of the pair of light beams. A signal representative of the direct reflectance of a light beam reflected from the surface into the photodetector is derived as a function of the focused and unfocused light.

BRIEF DESCRIPTION OF THE DRAWINGS

FIG. 3 is a plot showing a typical relationship between directly reflected light and scattered light as detected by a photodiode;

FIGS. 4A–4E are a series of plan views showing possible arrangements of light sources in a densitometer according to the present invention;

In the drawings, like reference numerals designate like elements, whether in physical views or schematic diagrams.

While the present invention will hereinafter be described in connection with a preferred embodiment and method of use thereof, it will be understood that it is not intended to limit the invention to that embodiment or method of use. On the contrary, it is intended to cover all alternatives, modifications and equivalents as may be included within the spirit and scope of the invention as defined by the appended claims.

DETAILED DESCRIPTION OF THE INVENTION

Figure 7:
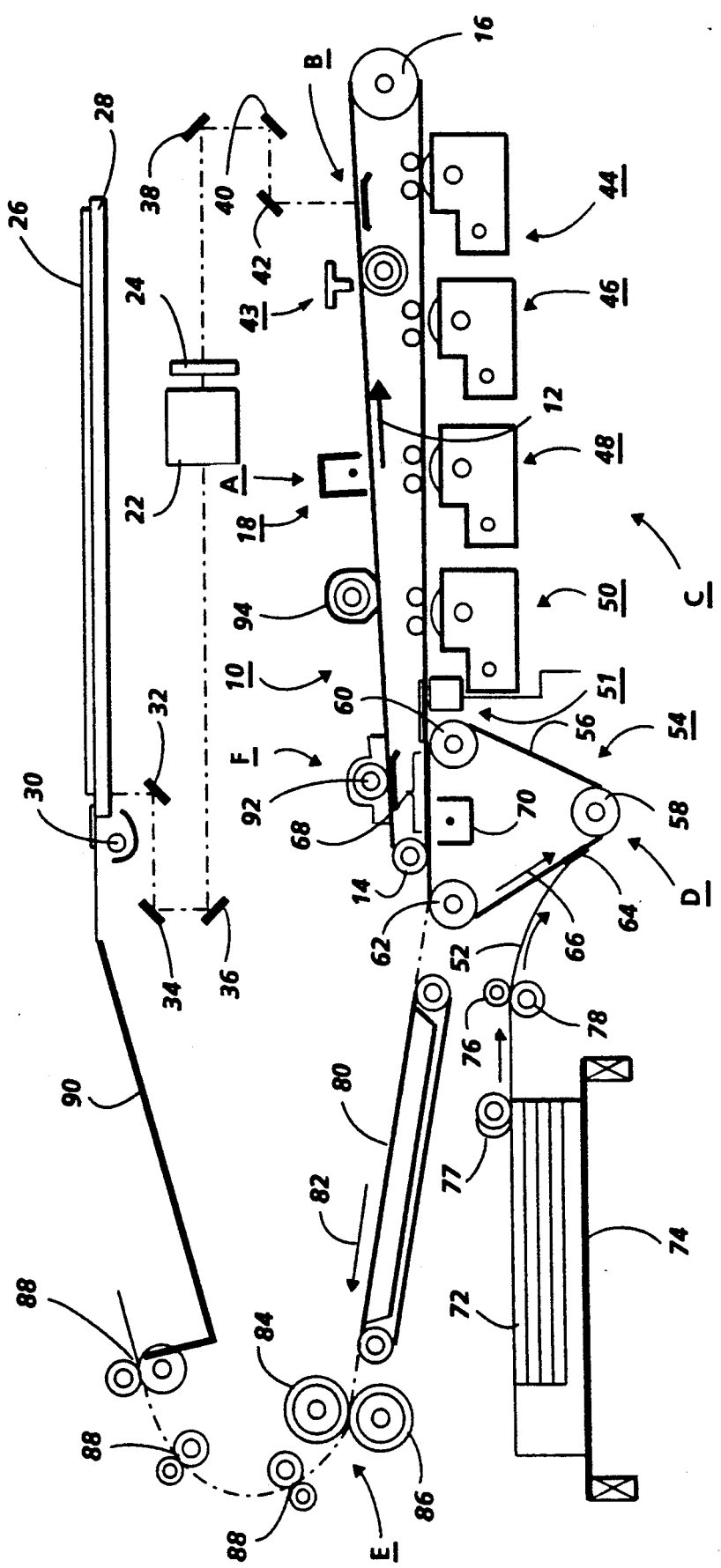
FIG. 7 is an elevational view of an electrophotographic printer.

FIG. 7 schematically depicts the various components of an illustrative electrophotographic printing machine incorporating the infrared densitometer of the present invention therein. It will become evident from the following discussion that the densitometer of the present invention is equally well suited for use in a wide variety of electrostatographic printing machines, and is not necessarily limited in its application to the particular electrophotographic printing machine shown herein.

Inasmuch as the art of electrophotographic printing is well known, the various processing stations employed in the FIG. 7 printing machine will be shown hereinafter schematically and their operation described briefly with reference thereto.

As shown in FIG. 7, the electrophotographic printing machine employs a photoreceptor belt 10. Preferably, the photoreceptor belt 10 is made from a photoconductive material coated on a grounding layer, which, in turn, is coated on an anti-curl backing layer. The photoconductive material is made from a transport layer coated on a generator layer. The transport layer transports positive charges from the generator layer. The interface layer is coated on the grounding layer. The transport layer contains small molecules of di-m-tolydiphenylbiphenyldiamine dispersed in a polycarbonate. The generation layer is made from trigonal selenium. The grounding layer is made from a titanium coated Mylar. The grounding layer is very thin and allows light to pass therethrough. Other suitable photoconductive materials, grounding layers, and anti-curl backing layers may also be employed. Belt 10 moves in the direction of arrow 12 to advance successive portions of the photoconductive surface sequentially through the various processing stations disposed about the path of movement thereof. Belt 10 is entrained about idler roller 14 and drive roller 16. Idler roller 14 is mounted rotatably so as to rotate with belt 10. Drive roller 16 is rotated by a motor coupled thereto by suitable means such as a belt drive. As roller 16 rotates, it advances belt 10 in the direction of arrow 12.

Initially, a portion of photoreceptor belt 10 passes through charging station A. At charging station A, a corona generating device, indicated generally by the reference numeral 18, charges photoreceptor belt 10 to a relatively high, substantially uniform potential.

Next, the charged photoreceptor surface is rotated to exposure station B. Exposure station B includes a moving lens system, generally designated by the reference numeral 22, and a color filter mechanism, shown generally by the reference numeral 24. An original document 26 is supported stationarily upon a transparent viewing platen 28. Successive incremental areas of the original document are illuminated by means of a moving lamp assembly, shown generally by the reference numeral 30. Mirrors 32, 34 and 36 reflect the light rays through lens 22. Lens 22 is adapted to scan successive areas of illumination of platen 28. The light rays from lens 22 are transmitted through filter 24 and reflected by mirrors 38, 40, and 42 on to the charged portion of photoreceptor belt 10. Lamp assembly 30, mirrors 32, 34 and 36, lens 22, and filter 24 are moved in a timed relationship with respect to the movement of photoreceptor belt 10 to produce a flowing light image of the original document on photoreceptor belt 10 in a non-distorted manner. During exposure, filter mechanism 24 interposes selected color filters into the optical light path of lens 22. The color filters operate on the light rays passing through the lens to record an electrostatic latent image, i.e. a latent electrostatic charge pattern, on the photoreceptor belt corresponding to a specific color of the flowing light image of the original document. Exposure station B also includes a test area generator, indicated generally by the reference numeral 43, comprising a light source to project a test light image onto the charged portion of the photoreceptor surface in the inter-image region, i.e. the region between successive electrostatic latent images recorded on photoreceptor belt 10, to record a test area. The test area, as well as the electrostatic latent image recorded on the photoreceptor surface of belt 10 are developed with toner particles at the development stations. One skilled in the art will appreciate that a RIS/ROS system may be used in lieu of the light-lens optical system descrived above.

After the electrostatic latent image and test area have been recorded on photoreceptor belt 10, belt 10 advances them to development station C. Development station C includes four individual developer units generally indicated by the reference numerals 44, 46, 48 and 50. The developer units are of a type generally referred to in the art as ."magnetic brush development units." Typically, a magnetic brush development system employs a magnetizable developer material including magnetic carrier granules having toner particles adhering triboelectrically thereto. The developer material is continually brought through a directional flux field to form a brush of developer material. The developer particles are continually moving so as to provide the brush consistently with fresh developer material. Development is achieved by bringing the brush of developer material into contact with the photoreceptor surface. Developer units 44, 46, and 48, respectively, apply toner particles of a specific color which corresponds to the compliment of the specific color separated electrostatic latent image recorded on the photoreceptor surface. The color of each of the toner particles is adapted to absorb light within a preselected spectral region of the electromagnetic wave spectrum corresponding to the wave length of light transmitted through the filter. For example, an electrostatic latent image formed by passing the light image through a green filter will record the red and blue portions of the spectrums as areas of relatively high charge density on photoreceptor belt 10, while the green light rays will pass through the filter and cause the charge density on the photoreceptor belt 10 to be reduced to a voltage level ineffective for development. The charged areas are then made visible by having developer unit 44 apply green absorbing (magenta) toner particles onto the electrostatic latent image recorded on photoreceptor belt 10. Similarly, a blue separation is developed by developer unit 46 with blue absorbing (yellow) toner particles, while the red separation is developed by developer unit 48 with red absorbing (cyan) toner particles. Developer unit 50 contains black toner particles and may be used to develop the electrostatic latent image formed from a black and white original document. The yellow, magenta and cyan toner particles are diffusely reflecting particles. Each of the developer units is moved into and out of the operative position. In the operative position, the magnetic brush is closely adjacent the photoreceptor belt, while, in the non-operative position, the magnetic brush is spaced therefrom. During development of each electrostatic latent image only one developer unit is in the operative position, the remaining developer units are in the non-operative position. This insures that each electrostatic latent image and successive test areas are developed with toner particles of the appropriate color without comingling. In FIG. 7, developer unit 44 is shown in the operative position with developer units 46, 48 and 50 being in the non-operative position. The developed test area passes beneath a densitometer, indicated generally by the reference numeral 51. Densitometer 51 is positioned adjacent the photoreceptor surface of belt 10 to generate electrical signals proportional to the developed toner mass of the test area. The detailed structure of densitometer 51 will be described hereinafter.

After development, the toner image is moved to transfer station D where the toner image is transferred to a sheet of support material 52, such as plain paper amongst others. At transfer station D, the sheet transport apparatus, indicated generally by the reference numeral 54, moves sheet 52 into contact with photoreceptor belt 10. Sheet transport 54 has a pair of spaced belts 56 entrained about three rolls 58, 60 and 62. A gripper 64 extends between belts 56 and moves in unison therewith. Sheet 52 is advanced from a stack of sheets 72 disposed on tray 74. Feed roll 77 advances the uppermost sheet from stack 72 into the nip defined by forwarding rollers 76 and 78. Forwarding rollers 76 and 78 advance sheet 52 to sheet transport 54. Sheet 52 is advanced by forwarding rollers 76 and 78 in synchronism with the movement of gripper 64. In this way, the leading edge of sheet 52 arrives at a preselected position to be received by the open gripper 64. The gripper then closes securing the sheet thereto for movement therewith in a recirculating path. The leading edge of the sheet is secured releasably by gripper 64. As the belts move in the direction of arrow 66, the sheet 52 moves into contact with the photoreceptor belt, in synchronism with the toner image developed thereon, at the transfer zone 68. A corona generating device 70 sprays ions onto the backside of the sheet so as to charge the sheet to the proper magnitude and polarity for attracting the toner image from photoreceptor belt 10 thereto. Sheet 52 remains secured to gripper 64 so as to move in a recirculating path for three cycles. In this way, three different color toner images are transferred to sheet 52 in superimposed registration with one another. Thus, the aforementioned steps of charging, exposing, developing, and transferring are repeated a plurality of cycles to form a multi-color copy of a colored original document.

After the last transfer operation, grippers 64 open and release sheet 52. Conveyor 80 transports sheet 52, in the direction of arrow 82, to fusing station E where the transferred image is permanently fused to sheet 52. Fusing station E includes a heated fuser roll 84 and a pressure roll 86. Sheet 52 passes through the nip defined by fuser roll 84 and pressure roll 86. The toner image contacts fuser roll 84 so as to be affixed to sheet 52. Thereafter, sheet 52 is advanced by forwarding roll pairs 88 to catch tray 90 for subsequent removal therefrom by the machine operator.

The last processing station in the direction of movement of belt 10, as indicated by arrow 12, is cleaning station F. A rotatably mounted fibrous brush 92 is positioned in cleaning station F and maintained in contact with photoreceptor belt 10 to remove residual toner particles remaining after the transfer operation. Thereafter, lamp 94 illuminates photoreceptor belt 10 to remove any residual charge remaining thereon prior to the start of the next successive cycle.

Figure 1:
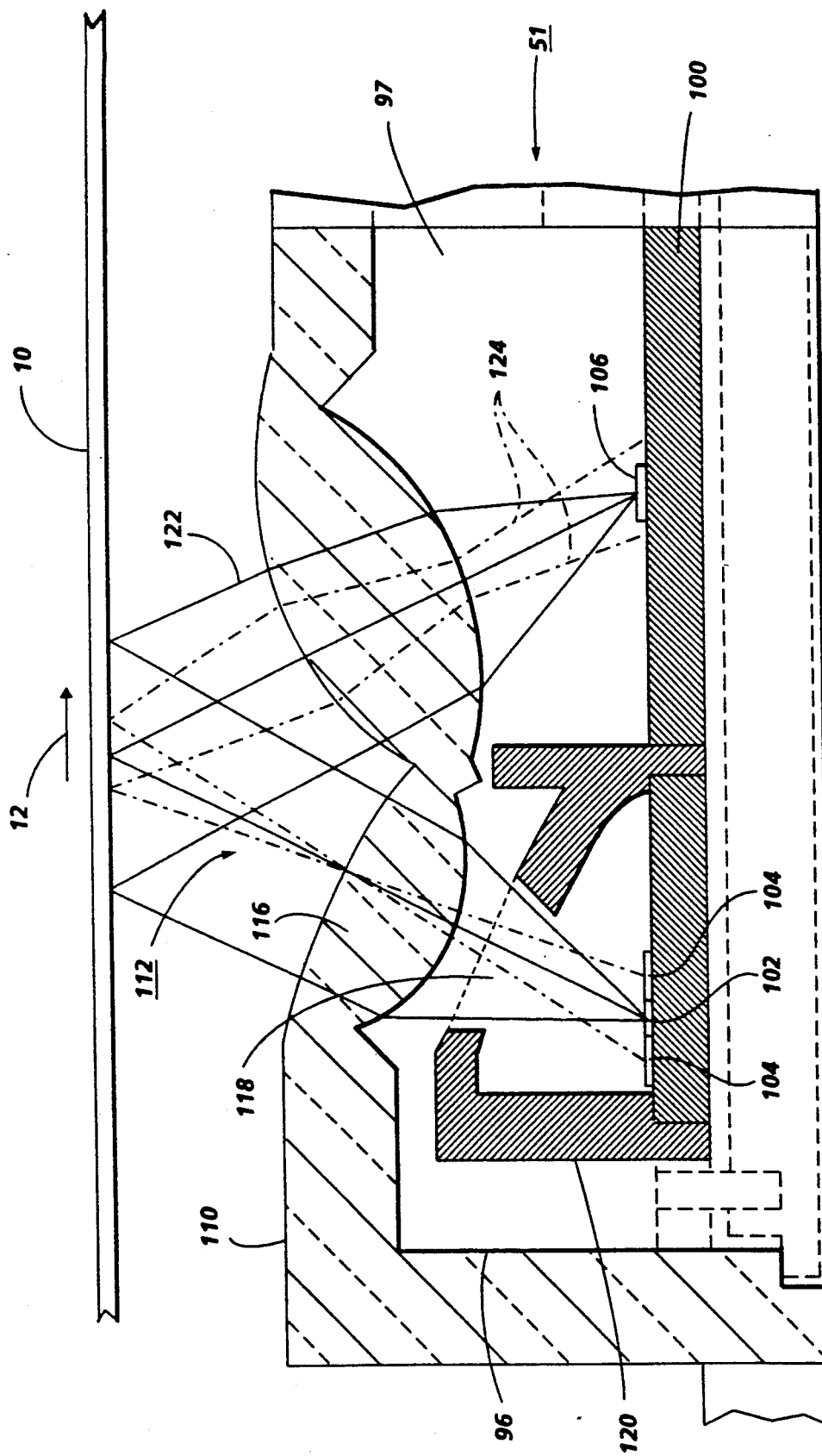
FIG. 1 is a sectional, elevational view of a densitometer according to the present invention.
Figure 2:
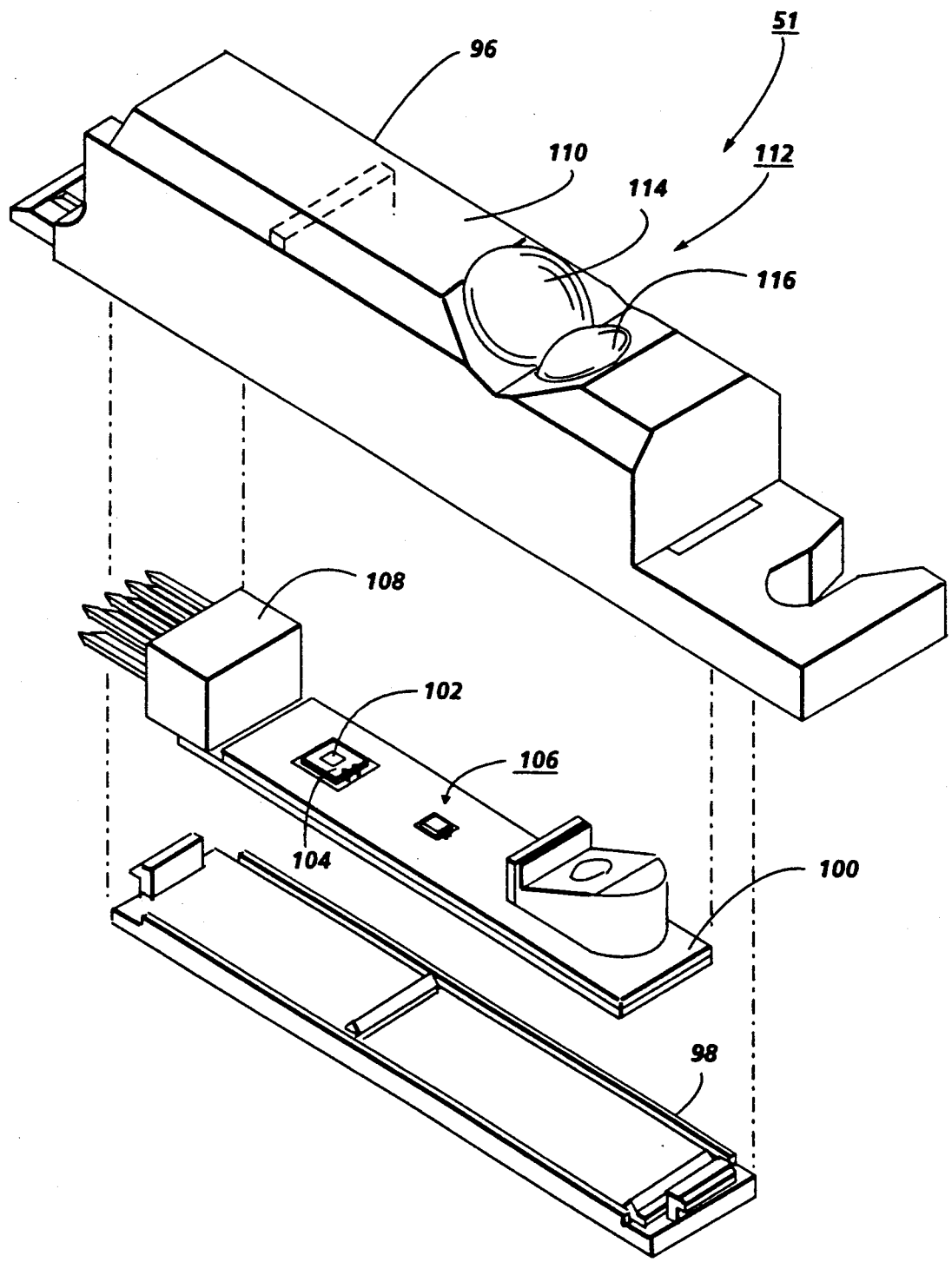
FIG. 2 is an exploded view of the densitometer of FIG. 1.

Referring now to FIGS. 1 and 2, there is shown infrared densitometer 51 in greater detail. Densitometer 51 includes a generally rectangularly shaped molded housing 96 made preferably from an acrylic material or any other suitable optically transparent material. Housing 96 defines a chamber 97. A cover 98 encloses the bottom of housing 96. A printed circuit wiring board 100 is mounted between cover 98 and housing 96 in chamber 97. Printed circuit board 100 supports a primary source, here in the form of light emitting diode (LED) 102 for providing light rays to illuminate the marking particles adhering to the photoreceptor surface of belt 10. Positioned adjacent primary source 102 is at least one secondary source 104, which operates independently of primary source 102. In the embodiment shown, there are shown two secondary sources, each marked 104, although numerous arrangements of secondary sources 104 relative to the primary source 102 are possible, as will be explained in detail below. A photodiode light sensing element 106 is also mounted on printed circuit board 100. Connector 108 is also mounted on printed circuit board 100. An integrated circuit (not shown) is electrically connected to primary source 102, secondary sources 104 and photodiode 106 to provide drive current to sources 102 and 104 and photodiode 106. The top surface 110 of housing 96 defines a V-shaped recess, generally indicated by the reference numeral 112. One surface of the V-shaped recess 112 supports a condenser lens 116 which is an integral collimating lens. The other surface of the V-shaped recess 112 supports another condenser lens 114 which is an integral collector lens. Further details of the structure of the densitometer, exclusive of secondary sources 104 and photodiode 106, may be found in U.S. Pat. No. 4,553,033, the relevant portions thereof being hereby incorporated into the present application.

Primary source 102 generates near infrared light rays which are transmitted through an aperture 118 in housing 120 onto condenser lens 116. Condenser lens 116 collimates the light rays and focuses the light rays onto the marking or toner particles deposited on the test area recorded on the surface of photoreceptor belt 10.

Secondary sources 104 also generate near infrared light rays, but because the secondary sources 104 are displaced a small distance from primary source 102, the light rays from secondary sources 104 are not focused directly through condenser lenses 114 and 116 onto photodiode 106, as are the light rays from primary source 102. However, the secondary sources 104 are sufficiently close to the primary source 102 such that light rays emitted by secondary sources 104 strike the surface of belt 10 in essentially the same general area as the rays from primary source 102, but only the scattered component of the returned light reaches photodiode 106. The relevent diffuse or scattered components of the light flux, shown by arrows 124, flood the area surrounding and including photodiode 106.

FIG. 3 is a plot showing the general relationship between reflected light, indicated as R, and scattered light, indicated as S, detected by a photodiode such as 106 as a function of toner coverage on a surface. The line indicated as R+S represents a sum of the values of R and S for different levels of toner coverage. It will be noted that, the greater the coverage of toner on the surface, the lower the intensity of reflected light R from the toner. On the other hand, as the toner coverage increases the reflectivity of the toner causing scattered reflected light, S, increases. Note also that the diffuse light scattered from a bare substrate, having no toner thereon, is not zero.

The present invention seeks to isolate the value of R from the value of R+S to obtain an accurate reading of toner coverage on a surface. As mentioned above, the value of R, corresponding to directly or specularly reflected light, is inversely related to the light absorption of toner on the surface of belt 10, which is a direct indication of toner density. Returning to FIG. 1, it can be seen that light emitted from primary LED 102 is focused through condenser lenses 114 and 116 in such a manner that the focal point of light emitted from primary LED 102 and reflected from surface 10 is more or less exactly on photodiode 106. Light rays so reflected and focused represent a value of R+S, illustrated in FIG. 3, associated with a given coverage of toner on the surface 10. The densitometer of the present invention obtains a value of R by sensing the difference between a measured value of R+S and a substantially simultaneous but separate measurement of the value of S, yielding an accurate measure of R.

In order to obtain the substantially simultaneous value of S, the secondary LEDs 104 are employed. Because the secondary LEDs 104 are not aligned with the condenser lenses 114 and 116 to focus light on photodiode 106, substantially none of the light emitted from secondary LEDs 104 and reflected on photoreceptor surface 10 will be focused on photodiode 106; that is, any light emitted from secondary LEDs 104 and subsequently detected by photodiode 106, because it is not directly reflected, will therefore be entirely scattered light, and thus entirely representative of S in the sum R+S. The value of R alone may be derived by taking the difference between this measured value of scattered light S and the value caused by direct reflection of light from primary LED 102 to photodiode 106, which is equal to R+S.

FIGS. 4A-4E are a series of plan views, showing a variety of possible spatial relationships among a primary source 102 and a set of secondary sources 104. As can be seen in FIGS. 4A-4E, the primary source 102, which may include one or more separate light emitting diodes (LEDs), is generally situated at the center of an arrangement of LEDs forming secondary source 104. FIG. 4E shows how a "ring source," designed to provide symmetric averaging of secondary illumination paths, can be made from a molded plastic annular light pipe surrounding the single LED of source 102, and illuminated from one or more external LEDs.

Figure 5:
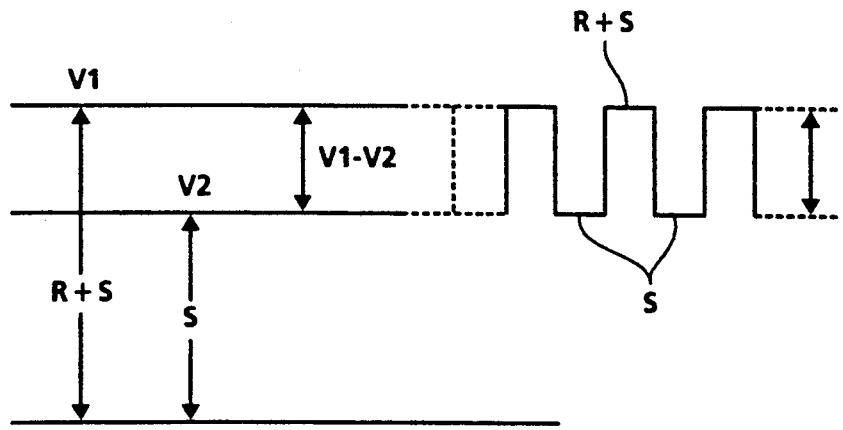
FIG. 5 is a signal diagram showing a typical output of a photodiode in a densitometer according to the present invention.

FIG. 5 illustrates the operation of the densitometer of the present invention, when primary source 102 and secondary sources 104 are operated in alternating manner to convey light rays to photodiode 106. In the preferred embodiment of the present invention, primary source 102 and secondary sources 104 are alternately switched on and off at a reasonably high rate, preferably on the order of 1000 cycles per second. That is, for the first part of a cycle only source 102 will be activated, and then for the second part of the cycle, only secondary sources 104 will be activated. FIG. 5 is a signal diagram showing an output of signals from photodiode 106 in response to this alternating operation of primary source 102 and secondary sources 104. In the portions of the cycle when primary source 102 is activated, the direct focusing of the light from source 102 (as shown by lines 122 in FIG. 1) will cause a relatively high voltage output from photodiode 106, shown as V1 in FIG. 5, and representative of the intensity of R+S (directly reflected light plus scattered light). In the second portion of each cycle, when secondary source 104 is activated, essentially no light rays will be directly focused onto photodiode 106, and any light detected by photodiode 106 will therefore be related entirely to scattered light (as shown by lines 124 in FIG. 1) and which represents S. The output from photodiode 106 in response to light rays from secondary sources 104, which is the same as the S scattered component, is given as voltage V2 in FIG. 5.

Since the value of V1 is representative of R+S and the output V2 is representative of S alone, it follows that V1−V2 represents a value of the R component alone, which is the most precise measurable value for determining toner area coverage. The alternating operation of primary source 102 and secondary sources 104 will result in the square-wave output shown in FIG. 5. The frequency of this output is necessarily the same as the frequency of the alternating activation of the light sources, and is thus preferably on the order of 1000 cycles per second. The absolute values of R+S and S may be designed into the system by selection of specific types of LEDs or other devices. Preferably, the relative intensities of sources 102 and 104 should be arranged such that the signals S and R+S detected at photodiode 106 are on exactly the same scale, making it easy to carry out the subtraction of S from R+S electronically.

Figure 6:
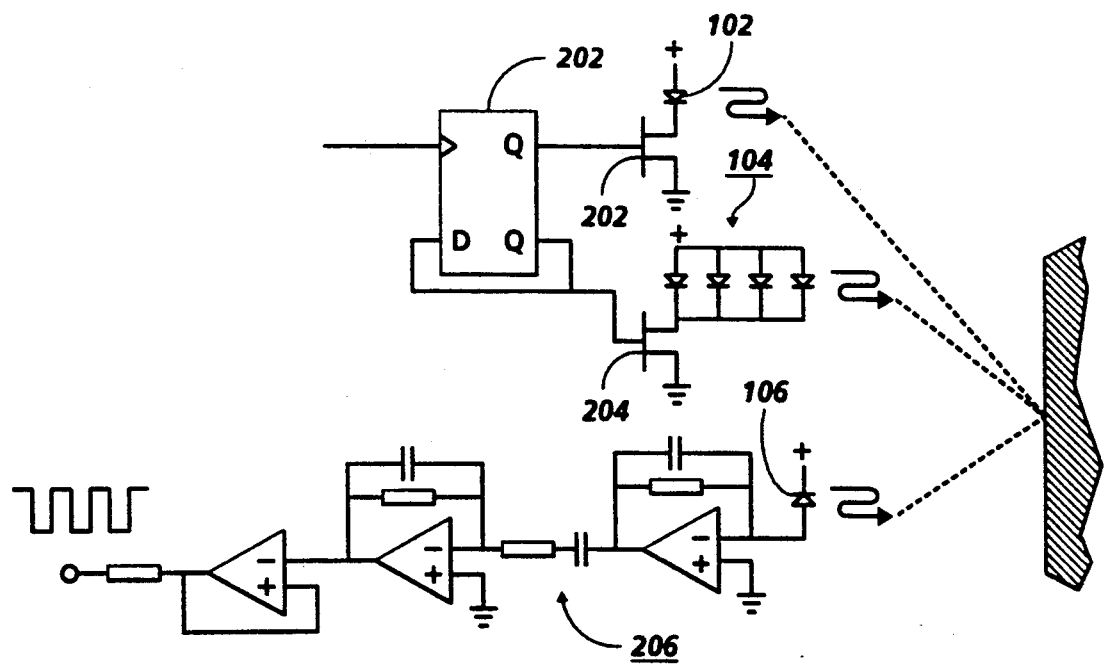
FIG. 6 is a schematic diagram of circuitry suitable for an embodiment of the present invention.

FIG. 6 is a schematic diagram of a simplified circuit for carrying out the alternating activation of sources 102 and 104, and also for detecting the light at photodiode 106 and separating the S component from the R+S signal. It will be understood that many alternate embodiments of an appropriate circuit may be apparent to one skilled in the art. Towards the top of FIG. 6 is the circuit for alternating activation of primary source 102, shown as a single LED 102, and secondary source 104, shown as an array of parallel of LEDs. Flip flop 200 is connected with its inverted output driving the D input so that it toggles state continuously with each clock transition CK from an external frequency source. Transistor switches 202 and 204 act as simple power drivers for the operation of sources 102 and 104, respectively, which may as necessary be directly connected to an external power source.

Light emitted from the LEDs associated with sources 102 and 104 strikes the sample area on photoreceptor belt 10 being measured and is then detected by photodiode 106 as indicated by dotted lines in FIG. 6. When the sources 102 and 104 are operated in an alternating manner the output of photodiode 106 will be generally in the form of a square wave. Photodiode 106 is shown connected to a two stage fixed gain AC amplifier circuit providing a stable analog output signal. Several different techniques can be employed to adjust the relative intensities of the signal associated with R+S and S, such as a simple potentiometer control that can be calibrated during manufacture. With the proper ratio of diode intensities applied, the amplitude of the square wave output V2−V1 itself is proportional to the difference (R+S)−S, and hence a direct measure of the desired value of R. The square wave signal can alternatively be processed through computer sampling of the sequential values of V1 and V2 by means of conventional analog-to-digital measurement techniques that will be evident to those skilled in the art, for effecting the numerical subtraction of V2 from V1 in a computer data acquisition system, leaving a difference value which may be interpreted as the R component of the reflected light into photodiode 106, which in turn can be used to derive an accurate measurement of the toner area coverage.

The advantage of using a relatively high frequency for operating the sources 102 and 104 is that, in the actual operation of an electrophotographic apparatus, wherein the photoreceptor belt 10 is moving at a relatively high speed, the high frequency of operation ensures that the densitometer can perform measurements of substantially the same small area (such as a test patch) on the photoreceptor belt as the photoreceptor belt 10 passes over the densitometer. Preferably, a number of distinct measurements of S and R+S, or a continuous burst of sequential values accumulated with every pass of the test patch may be taken, thus enabling data averaging which ensures more accurate and reliable result.

The alternating operation of sources 102 and 104, and the resultant square-wave generation of the output signal from phtodiode 106, are conducive to an AC-based design of the amplification system. The advantages of working with an effectively AC system, instead of a DC system, are well known. The differential nature of the sequential measurements effectively cancels any common mode response from unwanted inputs such as background light from other sources. It can also be appreciated that the gain of an AC signal can be made very high without most of the drift and stability problems usually associated with high gain DC amplification circuitry. Also, because the same amplifying system is used for both signals, circuit components need not be precisely matched and maintain long term stability as is the case when the S and R+S signals are individually amplified. Because the gain of an AC signal can be very high, the LED excitation power can be low and still yield a strong, unambiguous signal. Synchronous detection and integration systems can be employed to extract minute signals from a noisy background. On the whole, compared with the DC approach, fewer and cheaper components are needed to produce comparably accurate results.

While this invention has been described in conjunction with a specific apparatus, it is evident that many alternatives, modifications, and variations will be apparent to those skilled in the art. Accordingly, it is intended to embrace all such alternatives, modifications, and variations as fall within the spirit and broad scope of the appended claims.

What is claimed is:

1. An apparatus for measuring the reflectivity of a selected region of a surface, comprising:
    means for creating first and second light beams reflected from the selected region;
    a photodetector;
    a focusing lens positioned to focus the first light beam reflected from the selected region of the surface onto the photodetector through the axis of the focusing lens with the second light beam being reflected from the selected region and transmitted to the photodetector in a substantially unfocused manner; and
    processor means, operatively associated with the photodetector, for deriving a signal representative of the direct reflectance of a light beam reflected from the selected region of the surface into the photodetector as a function of the focused reflected light and the unfocused reflected light detected by the photodetector.

2. An apparatus as in claim 1, wherein the creating means comprises:
    a first light source for creating the first light beam; and
    a second light source for creating the second light beam.

3. An apparatus as in claim 2, wherein the photodetector is adapted to measure the intensity of infrared light.

4. An apparatus as in claim 2, further comprising a lens associated with the photodetector.

5. An apparatus as in claim 2, further comprising means for activating the first light source and the second light source in an alternating manner.

6. An apparatus as in claim 5, further comprising means for activating the first light source and the second light source in an alternating manner at a frequency from about 10 cycles per second to about 1000 cycles per second.

7. An apparatus as in claim 6, wherein the processor means is adapted to derive a signal representative of direct reflectance of a light beam from the selected region into the photodetector based on the difference between maxima and minima of a signal output by the photodetector as a result of the alternating activation of the first light source and the second light source.

8. An apparatus as in claim 2, wherein the second light source includes a plurality of light emitters arranged adjacent the first light source.

9. An apparatus as in claim 8, wherein the second light source includes a plurality of light emitters arranged substantially symmetrically relative to the first light source.

10. An apparatus as in claim 8, wherein the second light source includes a substantially circular light pipe disposed around the first light source.

11. A method for measuring the reflectivity of a selected region of a surface, comprising the steps of:
    reflecting a pair of light beams through a focusing lens from the selected region of the surface;
    detecting focused light from one of the pairs of light beams and unfocused light from the other of the pair of light beams; and
    deriving a signal representative of the direct reflectance of a light beam reflected from the surface into the photodetector as a function of the focused and unfocused light detected in the detecting step.

12. A method as in claim 11, wherein the light beams are of an infrared frequency.

13. A method as in claim 11, further comprising the step of reflecting each of the pair of light beams in an alternating manner.

14. A method as in claim 13, further comprising the step of reflecting each of the pair of light beams in an alternating manner at a frequency of about 10 cycles per second to about 1000 cycles per second.

15. A method as in claim 14, wherein the deriving step includes deriving a signal representative of direct reflectance of a light beam reflected from the surface a the photodetector as a function of the difference between maxima and minima of a signal output by the photodetector.

16. A method as in claim 14, further comprising the step of moving the surface relative to the photodetector during the activating step.

* * * * *